US009983146B1

(12) United States Patent
Fourie

(10) Patent No.: US 9,983,146 B1
(45) Date of Patent: May 29, 2018

(54) INSPECTION OF SEAL FOR HIGH ALTITUDE BALLOONS

(71) Applicant: X Development LLC, Mountain View, CA (US)

(72) Inventor: Daniel Henry Fourie, Sunnyvale, CA (US)

(73) Assignee: X Development LLC, Mountain View, CA (US)

( * ) Notice: Subject to any disclaimer, the term of this patent is extended or adjusted under 35 U.S.C. 154(b) by 0 days. days.

(21) Appl. No.: 15/597,374

(22) Filed: May 17, 2017

Related U.S. Application Data

(63) Continuation of application No. 14/811,189, filed on Jul. 28, 2015, now Pat. No. 9,689,808.

(51) Int. Cl.
*G01N 21/00* (2006.01)
*G01N 21/89* (2006.01)

(52) U.S. Cl.
CPC ..... *G01N 21/8901* (2013.01); *G01N 21/8914* (2013.01)

(58) Field of Classification Search
CPC ........ G01N 21/00; G01N 21/84; G01N 21/88; G01N 21/89; G01N 21/8901; G01N 21/8914; G01N 29/04; B31B 1/00
See application file for complete search history.

(56) References Cited

U.S. PATENT DOCUMENTS

| 1,763,109 | A | | 6/1930 | Strobl | |
|---|---|---|---|---|---|
| 3,047,252 | A | | 7/1962 | Huch et al. | |
| 4,877,205 | A | | 10/1989 | Rand | |
| 5,184,190 | A | * | 2/1993 | Rai ..................... | G01N 21/8901 250/559.12 |
| 5,488,480 | A | * | 1/1996 | Saindon ................... | B26D 5/20 250/559.4 |

* cited by examiner

*Primary Examiner* — Jamil Ahmed
(74) *Attorney, Agent, or Firm* — Lerner, David, Littenberg, Krumholz & Mentlik, LLP

(57) ABSTRACT

Aspects of the disclosure relate to systems and techniques for inspecting seals for high altitude balloons. In one example, a system may include a reflective surface, a translucent material on the reflective surface, and a movable light source configured to move along the reflective surface and provide light to the reflective surface. The light is provided such that it is reflected from the reflective surface and through the translucent material in order to backlight a balloon envelope seal for inspection. A method for inspecting a balloon envelope seal may include placing balloon envelope material on a table, forming a seal between portions of the material, moving a light over the seal, shining light onto a reflective portion of the table below the seal to backlight the seal, and inspecting the seal using the backlighting of the seal.

20 Claims, 9 Drawing Sheets

INSPECTION OF SEAL FOR HIGH ALTITUDE BALLOONS

CROSS-REFERENCE TO RELATED APPLICATIONS

The present application is a continuation of U.S. patent application Ser. No. 14/811,189, filed Jul. 28, 2015, the disclosure of which is incorporated herein by reference.

BACKGROUND

Computing devices such as personal computers, laptop computers, tablet computers, cellular phones, and countless types of Internet-capable devices are increasingly prevalent in numerous aspects of modem life. As such, the demand for data connectivity via the Internet, cellular data networks, and other such networks, is growing. However, there are many areas of the world where data connectivity is still unavailable, or if available, is unreliable and/or costly. Accordingly, additional network infrastructure is desirable.

Some systems may provide network access via a balloon network operating in the stratosphere. Because of the various forces experienced by these balloons during deployment and operation, there is a balancing of needs between flexibility and stability of materials. The balloons may be made of an envelope material configured in sections or lobes to create a "pumpkin" or lobed balloon. The lobes are supported by a plurality of tendons.

BRIEF SUMMARY

Aspects of the present disclosure relate to a system for inspecting seals for a balloon envelope. The system includes a reflective surface, a translucent material on the reflective surface, and a movable light source configured to move along the reflective surface and provide light to the reflective surface. The movable light source is configured such that light reflected from the reflective surface and through the translucent material in order to backlight a balloon envelope seal for inspection.

In one example, the movable light source is attached to a track such that the movable light source is movable along the track to provide light for inspection of the balloon envelope seal. In another example, the movable light source includes a housing having an open end and four walls arranged around the open end. Each of the four walls includes an end portion configured to press balloon envelope material against the translucent material and reduce the amount of light entering the housing which does not enter the housing through the translucent material. In another example, the movable light source includes a housing having an open end, a closed end, and one or more sidewalls arranged between the open end and the closed end. The closed end includes an image sensor configured to receive light reflected through the translucent material. In this example, the image sensor is a CCD configured to receive the light from the light source from the translucent material and generate an image of the seal. In addition or alternatively, the image sensor is configured to receive the light from the light source from the translucent material and send information about the seal to a computing device for processing. In this regard, the system also includes a computing device, wherein the computing device is configured to process the information about the seal and identify a problem with the seal. In another example, the system also includes the seal and the balloon envelope. In another example, the movable light source includes a housing having an open end, a closed end, and one or more sidewalls arranged between the open end and the closed end and at least one wing portion attached to the one or more sidewalls and a light source attached to the at least one wing. In this example, the light source includes an LED light strip. In addition, the at least one wing portion is arranged such that light from the light source travels through the translucent material, is reflected by the reflected surface back through the translucent material and into the open end of the housing. In another example, the system also includes a table, wherein the translucent material and the reflective surface are arranged on the table. In another example, the reflective surface is a mirror. In another example, the system also includes a heat sealer configured to move along a track and create the seal. The movable light source is attached to the heat sealer. In another example, the system also includes a heat sealer configured to move along a track and create the seal one portion at a time. The movable light source is configured to move along the track to backlight each portion of the seal. In another example, the movable light source includes an image sensor configured to send information to a computing device for processing. In another example, the movable light source is configured to receive instructions for moving along a track from a computing device. Another aspect of the disclosure provides a method of inspecting seals for a balloon envelope. The method includes placing balloon envelope material on a table, forming a seal between portions of the balloon envelope material, moving a movable light source over the seal, shining light from the movable light source onto a reflective portion of the table below the seal to backlight the seal, and inspecting the seal based using the backlighting of the seal.

In one example, the method also includes capturing light from the backlighting of the seal by an imaging device and sending information from the imaging device to a computing device for processing in order to inspect the seal. In another example, moving the movable light source includes moving the movable light source along a track positioned above the seal.

DETAILED DESCRIPTION

Figure 1:
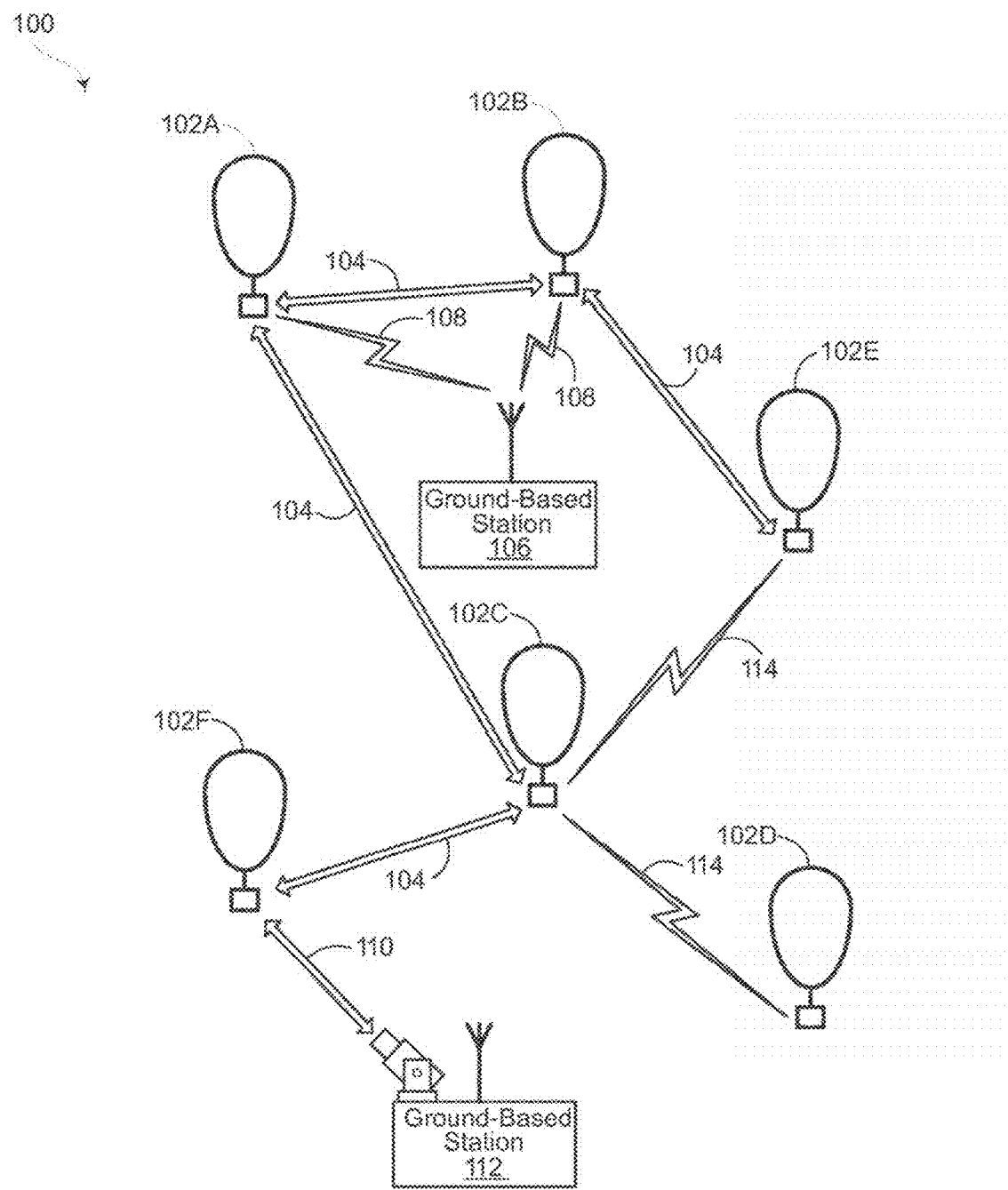
FIG. 1 is a functional diagram of a system in accordance with aspects of the present disclosure.

Aspects, features and advantages of the disclosure will be appreciated when considered with reference to the following description of embodiments and accompanying figures. The same reference numbers in different drawings may identify the same or similar elements. Furthermore, the following description is not limiting; the scope of the present technology is defined by the appended claims and equivalents. While certain processes in accordance with example embodiments are shown in the figures as occurring in a linear fashion, this is not a requirement unless expressly stated herein. Different processes may be performed in a different order or concurrently. Steps may also be added or omitted unless otherwise stated.

The present disclosure generally relates to providing high-altitude balloons such as those used in communication networks. A single network may include a large number of balloons, each of which includes a balloon envelope having a plurality of gores. In some examples, manufacturing of a single balloon envelope involves heat sealing portions of envelope material together in order to produce the gores. Given the nature of the use of these balloons and the resources needed to manufacture each balloon, it is important to maintain quality control of each balloon and in particular, the seals which hold together the gores. By doing so, this may significantly increase the likelihood of a successful launch and extend the life of the balloon.

To assemble a gore portion of a balloon envelope, portions of material which will form the gores are laid out on a table and then sealed together, for example, using a heat bond. This heat bond of the material can be employed using various techniques. In one example, a balloon gore sealing machine including a table and an overhead sealing component, may be used in order to at least partially automate the manufacturing process. The sealing component may be configured so that it can travel along a length of the table by traversing a track positioned above the table. The sealing component may apply a heat bonding seal in order to join together the portions in a downward pressing motion, one section at a time. In this example, the sealing component moves, seals and moves again until it completes a length of the balloon envelope made from bonding the portions together.

Once the sealing component has sealed a given portion of balloon envelope, the seal may be inspected for quality. To assist with the inspection, the seal may be backlit with a diffuse light. In some instances, the lighting may be integrated into the sealing surface of the table. This may provide a uniform background against which defects may be picked out. For a long stationary seal such as is found on a balloon gore, it may be expensive and complicated to install backlit lighting integrated into a surface along length of the table.

In another example, rather than backlighting the entire seal or an entire sealing surface of the table at once, a reflective surface may be used to backlight a seal. For instance, all or a portion of the table may include a reflective surface and a light may be positioned above the surface in order to reflect light. The reflected light may act as a back light and allow an observer to inspect the seal while the envelope material is on the table.

In other examples, rather than a human observing the reflected light directly, the inspection may be performed using an imaging device such as an image sensor. An image sensor may be configured to receive light rays from the light sources that are reflected from the mirror and through the silicone. For example, once a seal is completed, the image sensor may be positioned over the seal and lowered onto the envelope material. At least some of the light will be reflected through the seal, and eventually reach the imaging device. The light which reaches the imaging device may be processed in order to provide information about the seal, and in particular, the quality of the seal. Uniformity of the seal, and therefore the light passing through the seal may be indicative of a good seal.

The features described may provide for an efficient, economical way to inspect seal quality for high altitude balloons. In addition, by at least partially automating the inspection, this may increase consistency of the inspection and likelihood of detection of potentially problematic seals.

FIG. 1 depicts an example system 100 in which a balloon as described above may be used. This example should not be considered as limiting the scope of the disclosure or usefulness of the features of the present disclosure. For example, the techniques described herein can be employed on various types of standalone balloons or balloons used with other types of systems. In this example, system 100 may be considered a "balloon network." the system 100 includes a plurality of devices, such as balloons 102A-F, ground base stations 106 and 112 and links 104, 108, 110 and 114 that are used to facilitate intra-balloon communications as well as communications between the base stations and the balloons. One example of a balloon is discussed in greater detail below with reference to FIG. 2.

Figure 2:
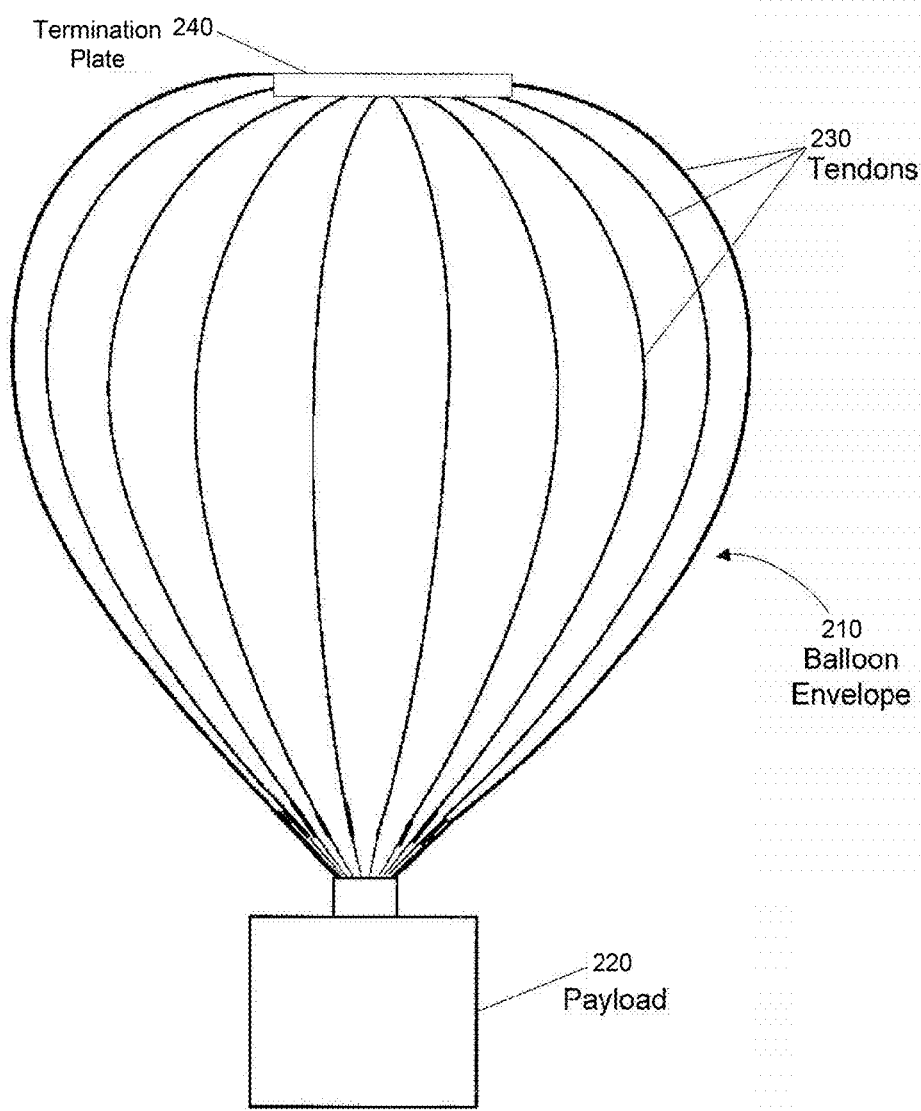
FIG. 2 is an example of a balloon in accordance with aspects of the present disclosure.

FIG. 2 is an example balloon 200, which may represent any of the balloons of balloon network 100. As shown, the balloon 200 includes an envelope 210, a payload 220 and a plurality of tendons 230, 240 and 250 attached to the envelope 210.

The balloon envelope 210 may take various forms. In one instance, the balloon envelope 210 may be constructed from materials such as polyethylene that do not hold much load while the balloon 200 is floating in the air during flight. Additionally, or alternatively, some or all of envelope 210 may be constructed from a highly flexible latex material or rubber material such as chloroprene. Other materials or combinations thereof may also be employed. Further, the shape and size of the envelope 210 may vary depending upon the particular implementation. Additionally, the envelope 210 may be filled with various gases or mixtures thereof, such as helium, hydrogen or any other lighter-than-air gas. The envelope 210 is thus arranged to have an associated upward buoyancy force during deployment of the payload 220.

The payload 220 of balloon 200 may be affixed to the envelope by a connection (not shown) such as a cable. The payload 220 may include a computer system (not shown), having one or more processors and on-board data storage. The payload 220 may also include various other types of equipment and systems (not shown) to provide a number of different functions. For example, the payload 220 may include an optical communication system, a navigation system, a positioning system, a lighting system, an altitude control system and a power supply to supply power to various components of balloon 200.

In view of the goal of making the balloon envelope 210 as lightweight as possible, it may be comprised of a plurality of envelope lobes or gores that have a thin film, such as polyethylene or polyethylene terephthalate, which is lightweight, yet has suitable strength properties for use as a balloon envelope. In this example, balloon envelope 210 is comprised of envelope gores 210A-210D.

Pressurized lift gas within the balloon envelope 210 may cause a force or load to be applied to the balloon 200. In that regard, the tendons 230 provide strength to the balloon 200 to carry the load created by the pressurized gas within the balloon envelope 210. In some examples, a cage of tendons (not shown) may be created using multiple tendons that are attached vertically and horizontally. Each tendon may be formed as a fiber load tape that is adhered to a respective envelope gore. Alternately, a tubular sleeve may be adhered to the respective envelopes with the tendon positioned within the tubular sleeve.

Top ends of the tendons 230 and 250 may be coupled together using an apparatus, such as termination plate 240 positioned at the apex of balloon envelope 210. Bottom ends of the tendons 230 may also be connected to one another. For example, a corresponding apparatus, e.g., base plate (not shown), may be disposed at a base or bottom of the balloon envelope 210. The termination plate 240 at the apex may be the same size and shape as and base plate at the bottom of the balloon envelope. Both plates may include corresponding components for attaching the tendons 230 to the balloon envelope 210.

In some examples, manufacturing of the balloon envelope involves heat sealing portions of envelope material together in order to produce the gores. For instance, portions of material which will form the gores may be laid out on a table and then sealed together, for example, using a heat bond. This heat bond of the material can be employed using various techniques.

Figure 3:
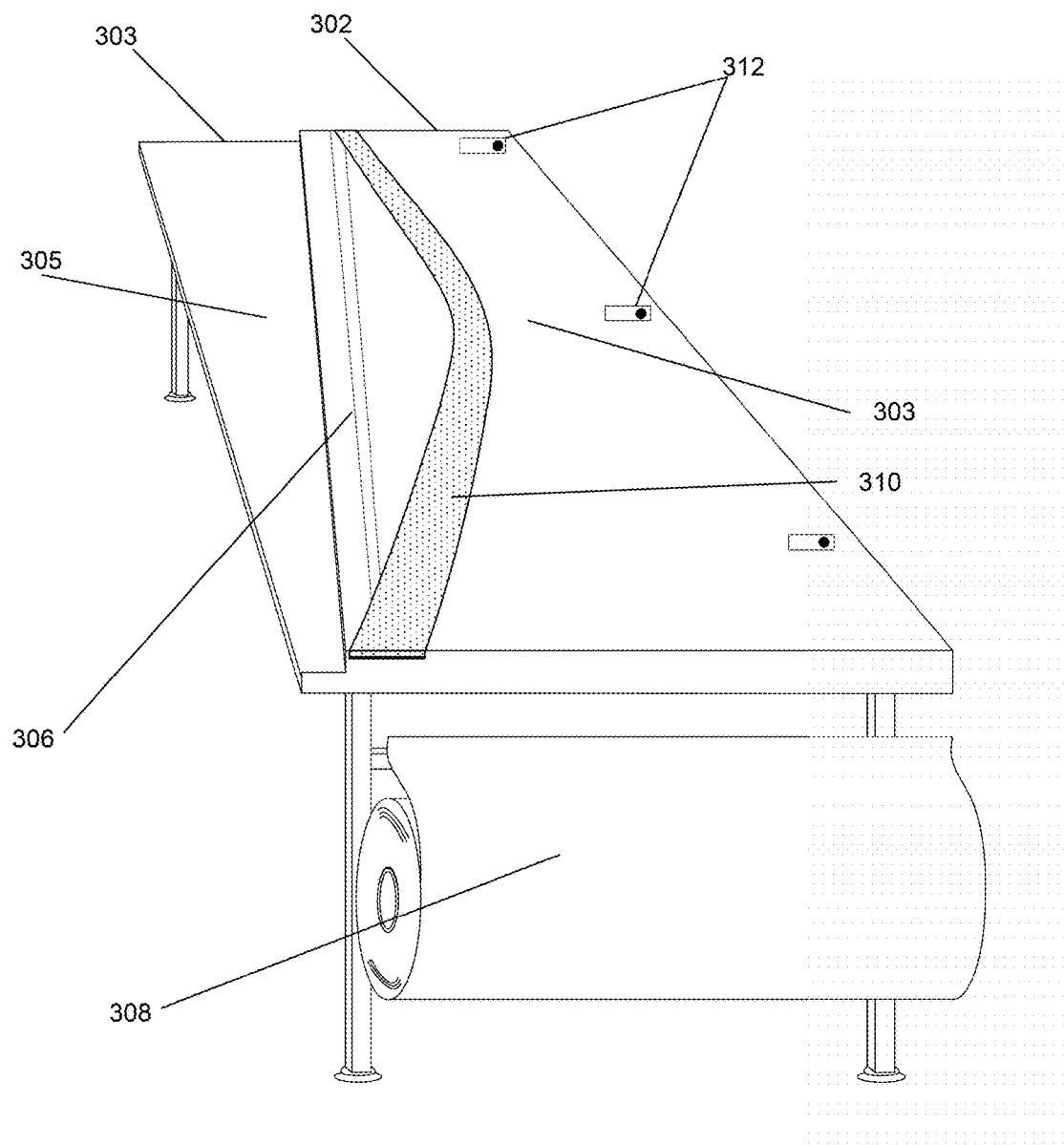
FIG. 3 is an example of a table component of a balloon gore manufacturing apparatus in accordance with aspects of the present disclosure.

In one example, a balloon gore sealing machine or assembly including a table may be used. In FIG. 3, one example of a table component 300 for the assembly is shown. As shown, the table component 300 includes a first level 302 and a second level 304 and an indicator 306 disposed on a surface 303 of the first level 302. The indicator 306 may be used to mark a position on the table component 300 for placing a tendon on an envelope gore being manufactured. The table component 300 made me used for shaping and heat-sealing together individual envelope gores made from sheets of balloon material 308 (shown as rolled). In this regard, the table component 300 also includes a curve strip 310 that can be used to indicate where the heat seal may occur, for example, at an edge of the envelope gore created from the roll of balloon material 308.

A sheet of the material 308 may be fed onto the table component 300 in order to create a given envelope gore. For example, a straight sheet of the balloon material 308 may be rolled out onto the table either manually or automatically using a belt driven track (not shown). Once the balloon material 308 is rolled out, it may be held down on the table component 300 using a series of restraints or clamps 312. The series of clamps 312 may help keep the balloon material 308 from shifting while it is being worked on.

First level 302 may be a working area of the table component 300. The first level 302 may include a smooth top layer of a compliant material, such as fiberglass and/or silicone, or other types of types of similar materials that have a level of heat resilience. The table component 300 may include also additional heat resistant material where the heat seal occurs, such as at curve strip 310. The curve strip 310 may include additional material, such as fiberglass impregnated with a polytetrafluoroethylene (PTFE) coating, which has a higher melting point than the top layer coating of the table component 300. This extra coating may also help prevent the material 308 from sticking to the table component 300 due do the heat sealing being conducted at the strip 310.

Second level 304 of the table component 300 may be configured for stacking up assembled envelope gores of the balloon envelope. For example, the second level 304 may include a trough like resting area for holding the envelope gores during manufacture. A surface 305 of the second level 304 may be configured so that the surface is wide enough to stack up a plurality of assembled envelope gores including the tendon attached to each gore portion.

Figure 4:
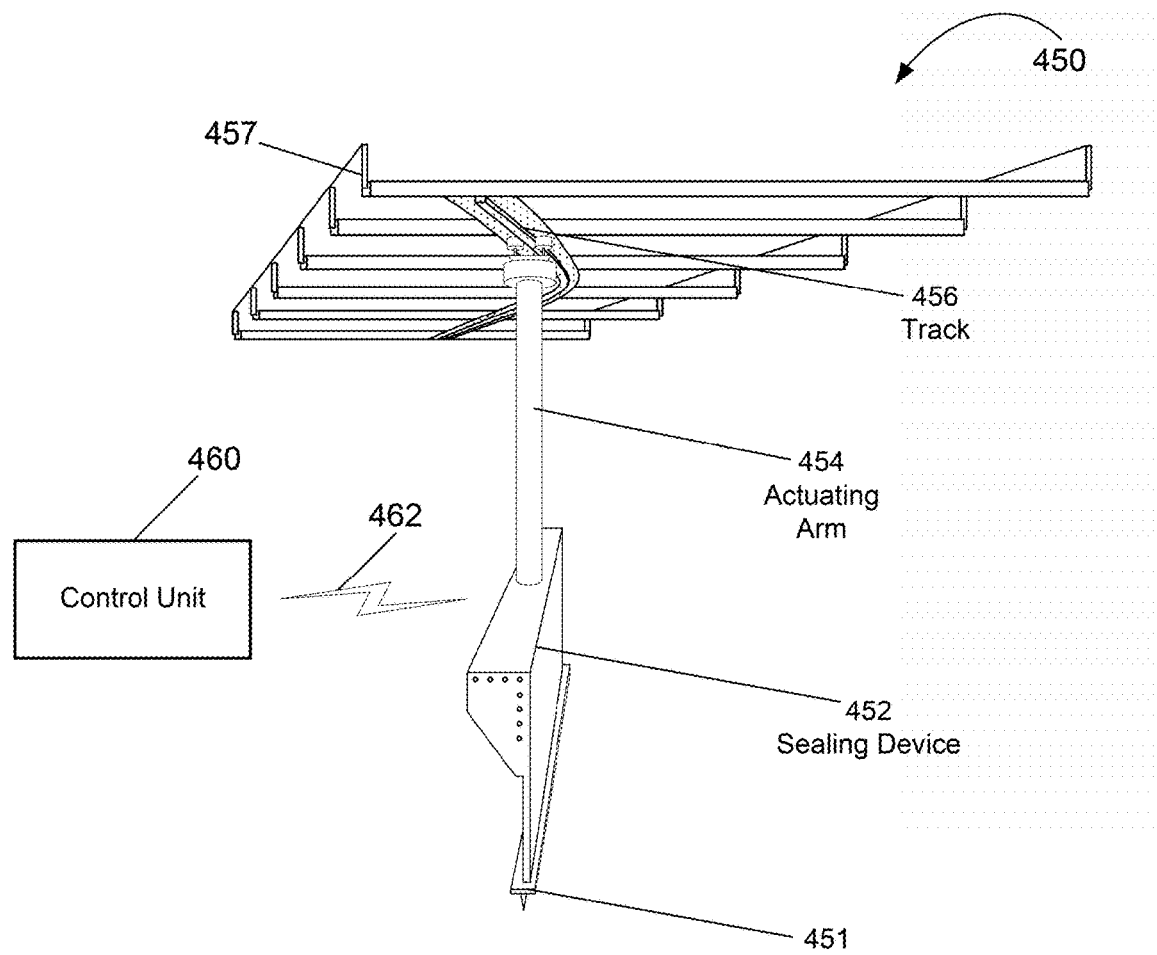
FIG. 4 is an example of a heat sealer component of a balloon gore manufacturing apparatus in accordance with aspects of the present disclosure.

An overhead heat sealer may be used in order to at least partially automate the manufacturing process. FIG. 4 is an example of a heat sealing component 450 for the assembly. In this example, the sealing component 450 includes a sealing device 452 coupled to the track 456 via an actuating arm 454. In some examples, a control unit 460 may be utilized for controlling operations of the sealing component 450 using communication link 462, which can be a wired or wireless link.

Sealing device 452 may include an electrically heatable element 451 disposed on the device. The heatable element 451 may be of a predetermined width and length that may be used to unite layers of the balloon material. For example, the heatable element 451, when activated, for example by a flow of electricity, may reach a certain temperature that is hot enough to heat bond or otherwise melting a section of two sheets of balloon material together. In some embodiments, sealing device 452 may provide a combination of operations for heat sealing and cutting of the balloon material 308. For example, the sealing device 452 may be configured to cut the balloon material 308 by using heat and an amount of pressure or blade like cutting members (not shown) attached to the heatable element 451.

The sealing component 450 may be configured so that it can travel along a length of the table by traversing a track positioned above the table. For example, sealing device 452 may be moved along track 456 mounted on an overhead support 457. The track 456 can be configured so that sealing device 452 can move forward and back horizontally by using actuating arm 454. This forward and back movement of the sealing device 452 along track 456 can be manually or automatically operated, for example, by using commands from the control unit 460.

The actuating arm 454 can also be activated to cause the sealing device 452 to move vertically. For example, the actuating arm 454 may include housing (not shown) that can extend and retract the arm between first and second positions. In some aspects, extension of the actuating arm 454 allows the sealing device 452 to be pressed against the balloon material in order to cause the heat bond activation. As with the movement along track 456, the actuating arm 454 can extend and/or retract manually, automatically or some combination thereof, for example, by using commands from control unit 460.

Figure 5:
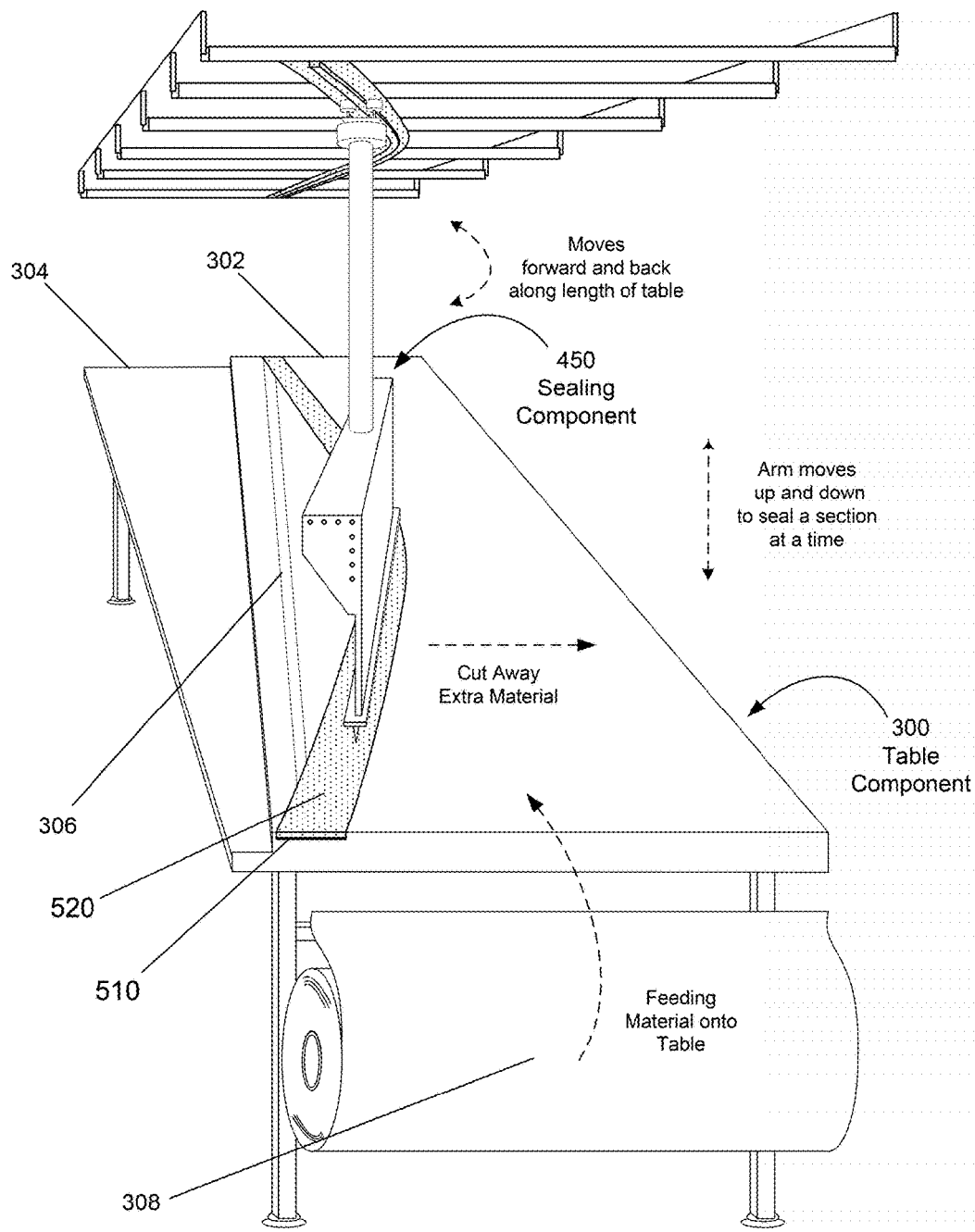
FIG. 5 is an example of a balloon gore manufacturing apparatus in accordance with aspects of the present disclosure.

FIG. 5 is an example of a balloon gore sealing assembly 500, which may include machinery components such as the table component 300 and sealing component 400 as described above. The assembly 500 may be used to manufacture envelope gores for balloons. To join the sheets of film material together, sealing component 450 may move forward and back from one end of table component 300 to an opposite end, thereby traversing along a length of the table component 300. The sealing component 450 may operate by heat sealing a section, for example by one meter more or less in length, of the balloon envelope material 308 resting on the first level. For example, sealing component 450 may be pressed down on the table component 300 for heating sealing a particular section of the envelope gore material and subsequently lifted up and moved to a next section to be heat sealed. This up, move and down motion of the sealing component 450 can be repeated until the entire length of the laid out material is heat sealed in successive sections resulting in a completed envelope gore. The process of manufacturing envelope gores can be repeated with the successive sheets of material 3408 until a sufficient number of gores have been manufactured.

Once the sealing component 450 has sealed a given portion of balloon envelope, the seal may be inspected for quality. In some examples, the inspection may be performed immediately after a seal is completed. This may involve a manual inspection (by an operator) or may be partially or fully automated. For example, a seal may be inspected to insure that the seal was fully formed (i.e. there are no gaps along the seal), that the envelope material is properly arranged (i.e. there are no unintentional folds or gathers in the material), that no debris is within the seal, etc. As an example, a good seal should appear to be uniform along the length of the seal.

To assist with the inspection, the seal may be backlit with a diffuse light. In some instances, the lighting may be integrated into the sealing surface of the table. This may provide a uniform background against which defects may be picked out. For a long stationary seal such as is found on a balloon gore, it may be expensive and complicated to install backlit lighting integrated into a surface along length of the table.

In another example, rather than backlighting the entire seal or the entire sealing surface of the table at once, a reflective surface may be used to backlight a seal. For instance, all or a portion of the table may include a reflective surface 520 (more clearly shown in FIG. 7) and a light may be positioned above the surface. The reflective surface 520 may include a mirror or mirror finish may be applied to the table on which the heat seals will be made. In addition, a layer 510 of translucent material, such as silicone, may be placed on top of the mirror to form the sealing surface and to better facilitate the heat sealing process. This layer may thus correspond to the curve strip 310 of the table component 300. The mirror may be used to reflect light from above the surface of the table through the silicone and the seal. The reflected light may act as a back light and allow an observer to inspect the seal while the envelope material 308 is on the table component.

Figure 6:
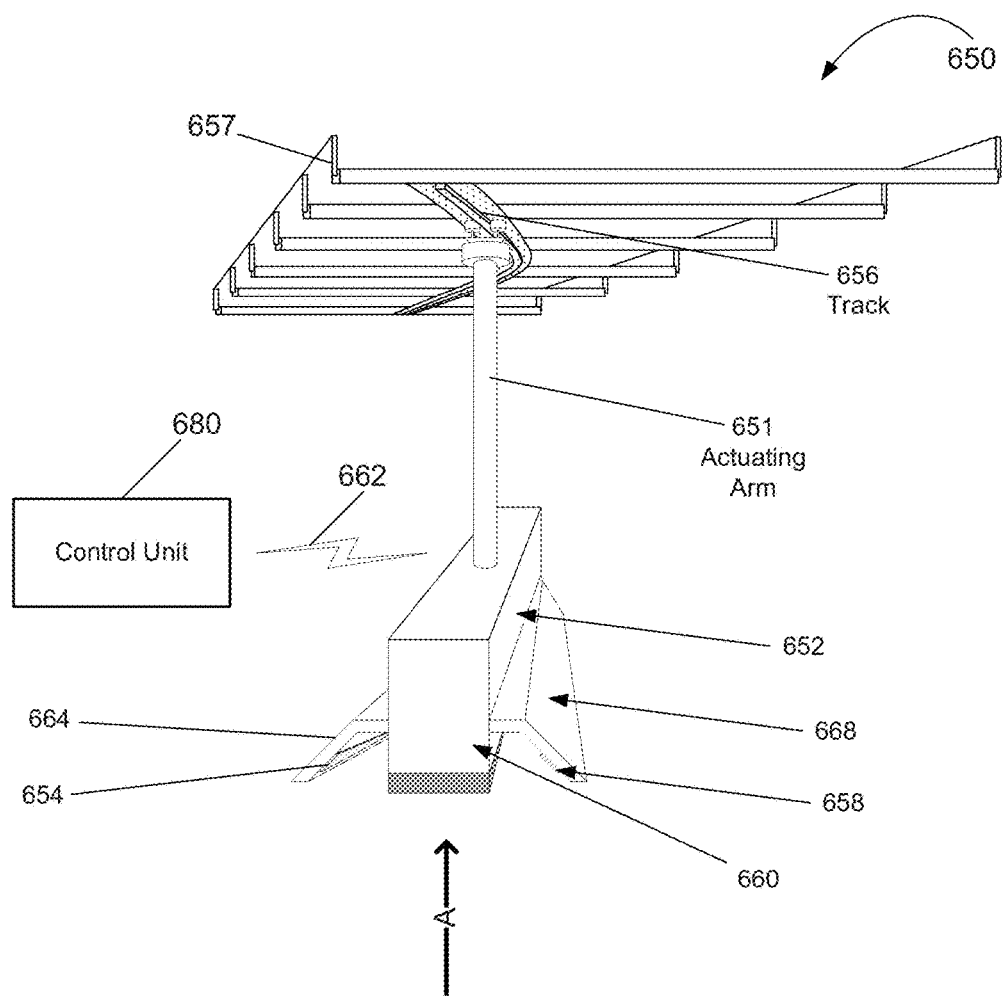
FIG. 6 is an example of aspects of a lighting system in accordance with aspects of the present disclosure.

In some examples, a light source may be incorporated into a lighting system that is attached to or separate from the sealing component 450. FIG. 6 is an example of aspects of a lighting system 650. The lighting system may include a movable inspection device 652 including the light source. In this example light sources 654 and 658 are incorporated into respective wing portions 664 and 668 which are attached to a housing 660. The movable inspection device may be automated and follow the same or a similarly arranged track as the sealing component 450. As shown in the example of FIG. 6, lighting system 650 is depicted as separate from sealing component 450. However, in some examples, movable inspection device 652 may be attached to or simply placed adjacent to sealing component 450 during operation.

In some examples, a control unit 680 may be utilized for controlling operations of the light system 650 using communication link 662, which can be a wired or wireless link. In this regard, the control unit 680 and communication link 662 may be the same or similarly configured as control unit 460 and communication link 662.

Track 656 may correspond to track 456. In this way, lighting system 650 may be configured so that it can travel along a length of the table by traversing a track positioned above the table. For example, housing 650 may be moved along track 656 mounted on an overhead support 657. As with track 456 and sealing component 450, track 656 can be configured so that lighting system 650 can move forward and back horizontally by using actuating arm 6541. This forward and back movement of the housing 650 along track 656 can be manually or automatically operated, for example, by using commands from the control unit 460.

In other examples, track 656 may be the same track as 657. Thus, once the sealing component 450 has completed a seal and moves onto the next seal location, the movable inspection device 652 may follow immediately behind the sealing component 450 on track 656/456 and light the seal.

As with actuating arm 454, actuating arm 654 can also be activated to cause the housing 652 to move vertically. For example, the actuating arm 6541 may include housing (not shown) that can extend and retract the arm between first and second positions. In some aspects, extension of the actuating arm 651 allows the housing 652 to be pressed against the balloon material 308 during inspection. As with the movement along track 652, the actuating arm 651 can extend and/or retract manually, automatically or some combination thereof, for example, by using commands from control unit 680.

Figure 7:
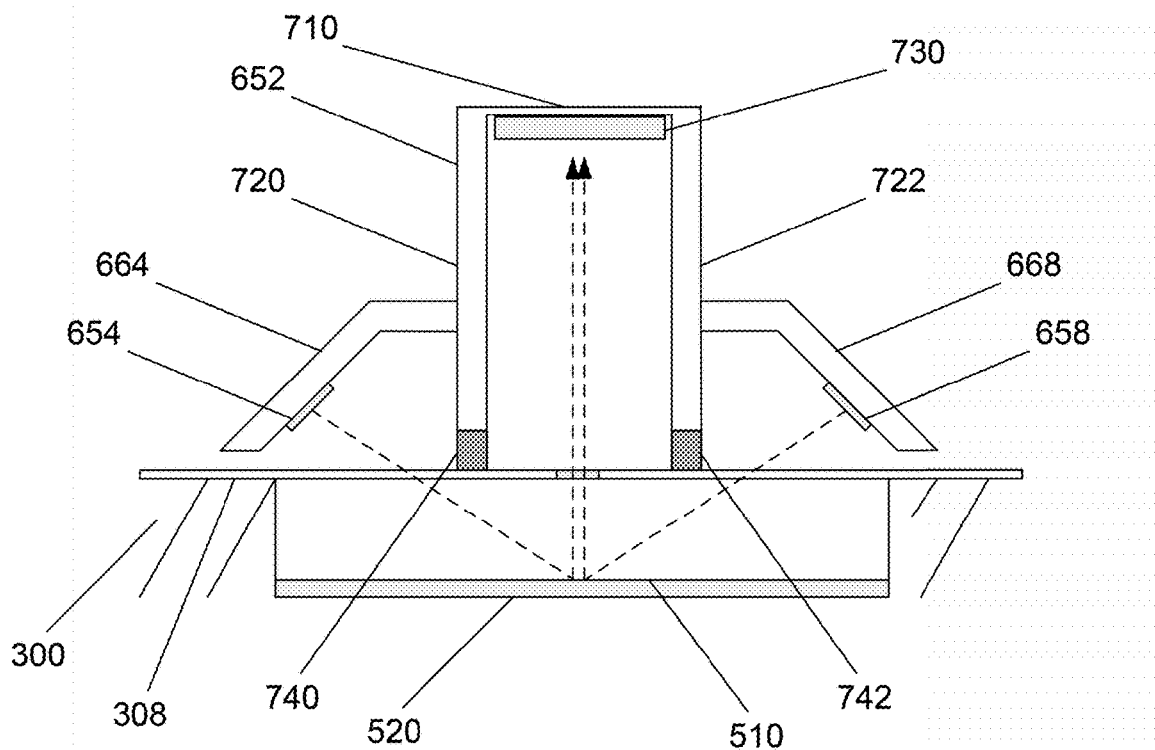
FIG. 7 is an example view of portions of a movable inspection device and table in accordance with aspects of the present disclosure.
Figure 8:
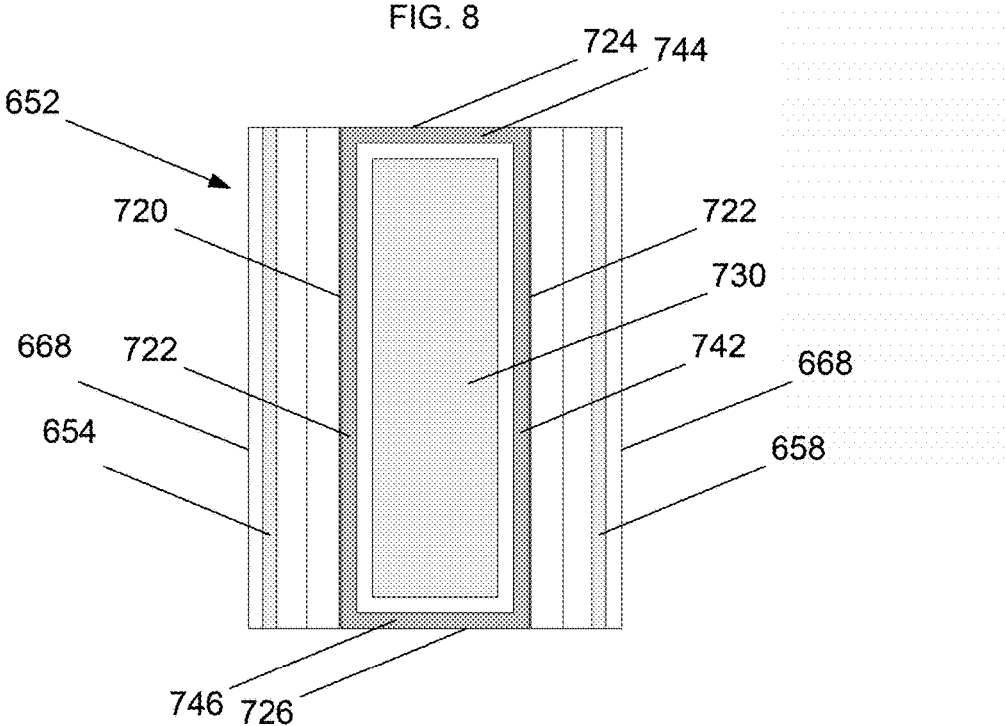
FIG. 8 is an example view of portions of a movable inspection device in accordance with aspects of the present disclosure.
Figure 9:
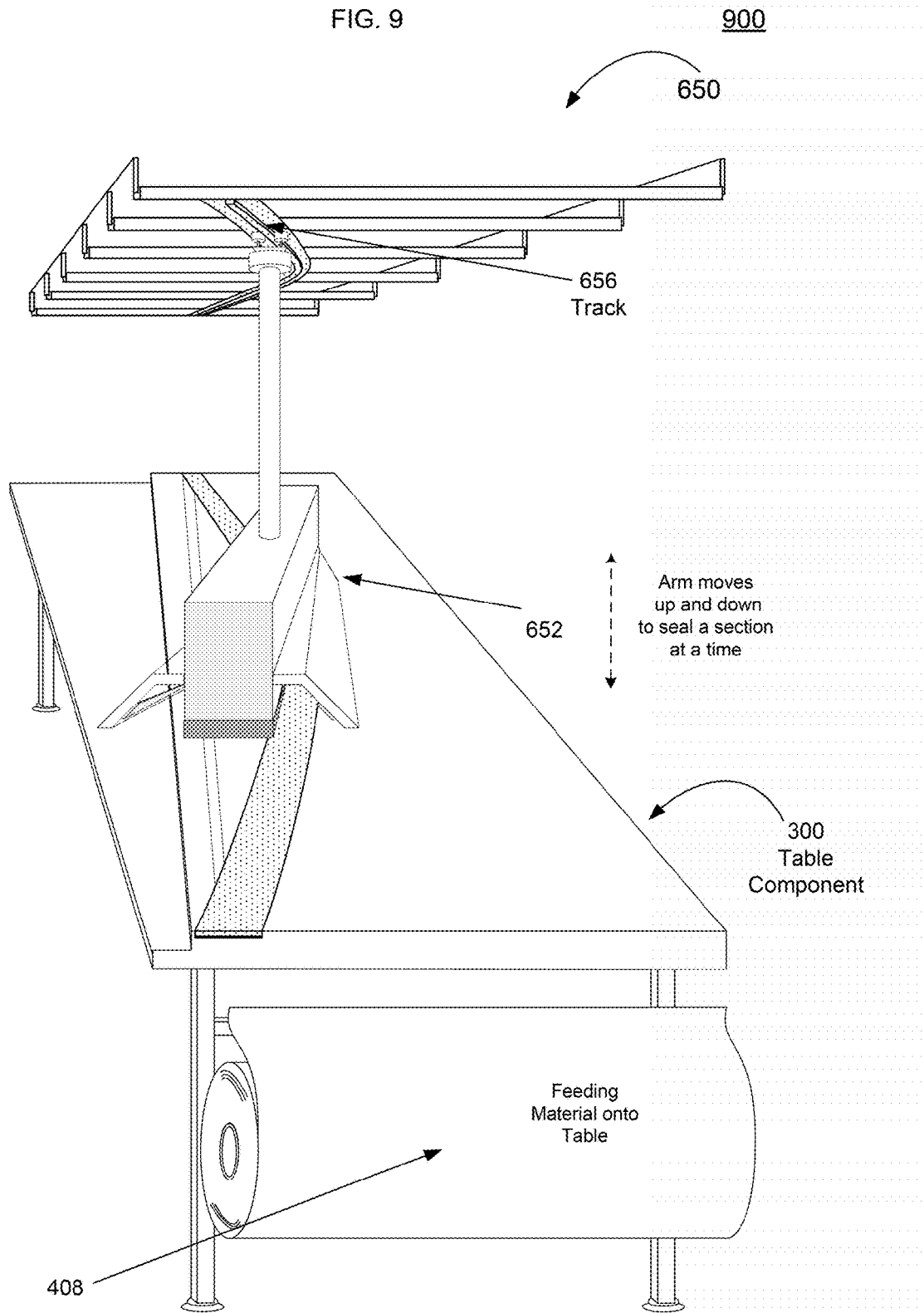
FIG. 9 is an example of aspects of a lighting system in accordance with aspects of the present disclosure.
Figure 10:
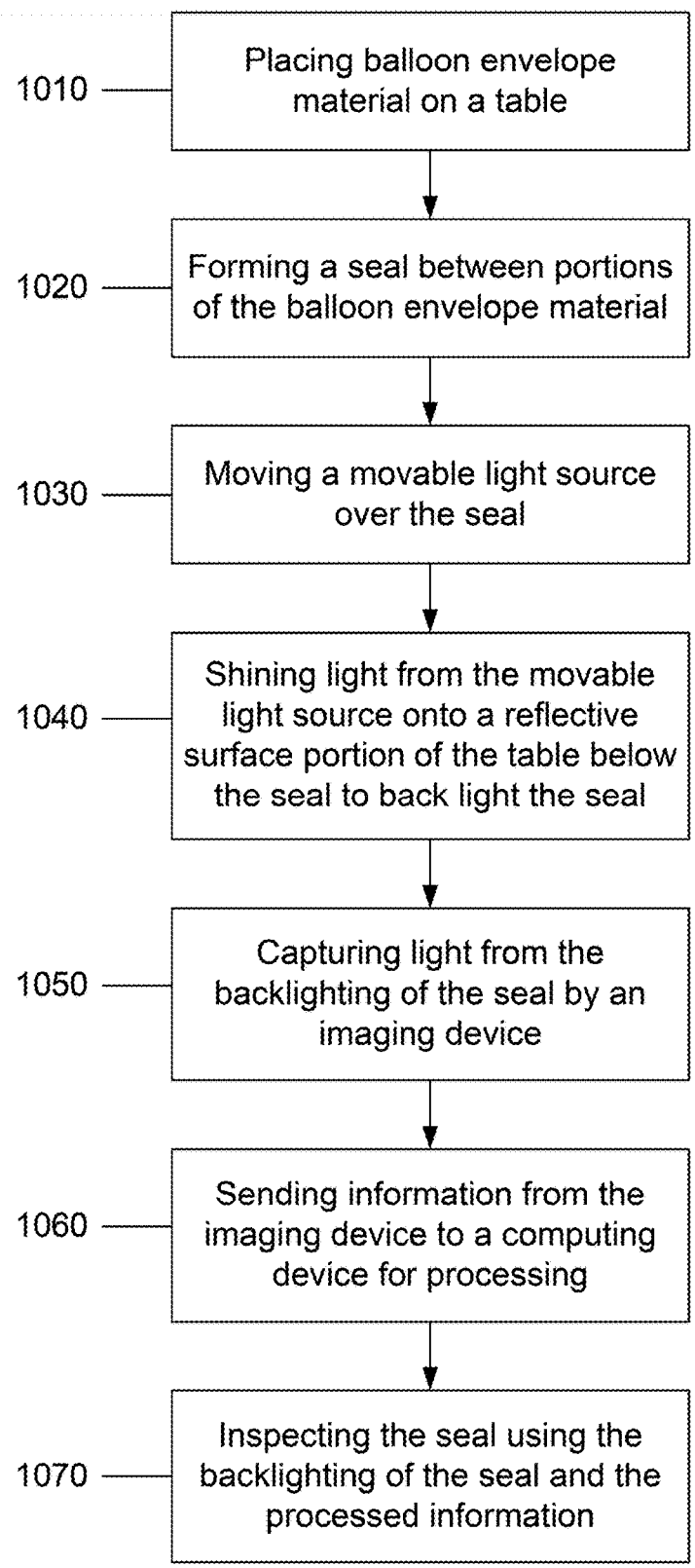
FIG. 10 is a flow diagram depicting an example of a method in accordance with aspects of the present disclosure.

In other examples, rather than a human observing the reflected light directly, the inspection may be performed using an imaging device. FIG. 7 is a cross sectional view of the housing 652 shown in a configuration where the housing is pressed against the table component 300 during an inspection of the seal. FIG. 8 is a view from the perspective of arrow A in FIG. 6 in order to illustrate the internal configuration of the housing 652. FIG. 9 is an example 900 of lighting system 650 depicted above the table component 300. For simplicity, sealing component 450 is not shown, but may also hang from track 656 (here, the same as track 456) adjacent to the movable inspection device 652 via the actuating arm 454.

In the examples of FIGS. 7-9, the housing 652 includes a top portion 710 and four walls 720, 722, 724, 726 (best shown in FIG. 8) that extend away from the top portion. As noted above, two wing portions 664 and 668 each including a respective light source 654 and 658 are attached to the housing 660 at a preselected angle. The light sources may include LED light strips. The angle may be preselected to ensure that adequate light from the light sources will be reflected off of the reflective surface 520 and back to an imaging device. The top portion of the housing may include an imaging device 730 mounted thereon.

The imaging device 730 may include a camera or charge coupled device (CCD) image sensor. An end portion of each wall includes a respective seal portion 740, 742, 744, 746. These seal portions may be configured to press envelope material 308 against the layer 510 of translucent material of the table component 300 and prevent light from hitting a surface of the layer 510 from within the housing 660 below the imaging device.

The imaging device 730 may be configured to receive light rays from the light sources 654 and 658 that are reflected from the reflective surface 520 and through the layer 510. For example, once a seal is completed, the housing 652 may be positioned over the seal and lowered onto the envelope material 308 using actuating arm 651. The seal portions 740, 742, 744, 746 of the walls 720, 722, 724, and 726 then press the envelope material 308 against the layer 510 sealing out any light which would come from within the housing.

Light rays from the light sources 654 and 656 may then shine through the layer 510 and onto the reflective surface 520. At least some of the light rays will be reflected through the layer 510, through the seal, and eventually reach the imaging device 730. The amount of light that reaches the imaging device 730 is related to the preselected angle of the wing portions 664 and 668 as well as the position of and amount of light generated by the light sources 654 and 656. The light which reaches the imaging device may be processed in order to provide information about the seal, and in particular, the quality of the seal. Again, uniformity of the seal, and therefore the light passing through the seal may be indicative of a good seal.

To better aid in understanding an example of some of the aspects described above, reference is now made to FIG. 11, which illustrates a flow diagram 1000 depicting a method of manufacturing a balloon envelope. As previously discussed, the following operations do not have to be performed in the precise order described below. Rather, as mentioned above, various operations can be handled in a different order or simultaneously, and operations may be added or omitted.

In this example, balloon envelope material is placed on a table at block 1010. A seal is formed between portions of the balloon envelope material at block 1020. A movable light source is moved over the seal at block 1030. This may include moving the movable light source along a track positioned above the seal. Light is shined from the moveable light source onto a reflective surface portion of the table below the seal to backlight the seal at block 1040. Light from the backlighting of the seal is captured by an imaging device at block 1050. Information from the imaging device is sent to a computing device for processing at block 1060. And, at block 1070, the seal is inspected using the backlighting of the seal and the processed information.

Most of the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. As an example, the preceding operations do not have to be performed in the precise order described above. Rather, various steps can be handled in a different order or simultaneously. Steps can also be omitted unless otherwise stated. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements.

The invention claimed is:

1. A system for inspecting seals between one or more pieces of translucent material, the system comprising:
   an inspection device having:
      a housing including one or more sidewalls forming an enclosure having a closed end and an open end, the housing having at least one wing portion extending away from the housing from an outer surface of one of the one or more sidewalls at an angle such that a first side surface of the at least one wing is oriented away from the one or more sidewalls and a second side surface of the at least one wing is oriented towards the one or more sidewalls;
      a light source arranged on the second side surface; and
      an image sensor arranged on the closed end such that the light sensor sits within the enclosure.

2. The system of claim 1, further comprising a control unit configured to control operations of the inspection device.

3. The system of claim 1, further comprising an actuating arm configured to extend and retract the inspection device.

4. The system of claim 3, further comprising a control unit configured to control extension and retraction of the arm in order to move the housing towards and away from a seal for inspection.

5. The system of claim 3, wherein the arm is further configured to allow the housing to be pressed against a surface.

6. The system of claim 1, wherein the image sensor includes a charge coupled device.

7. The system of claim 1, wherein the image sensor is configured to receive light from the light source that has been reflected off of another object towards the image sensor.

8. The system of claim 1, wherein each of the one or more sidewalls includes an end portion configured as a seal portion arranged to prevent light from entering the enclosure between the seal portion and a surface when the one or more sidewalls are pressed against the surface.

9. The system of claim 1, wherein the one or more sidewalls are arranged as four connected sidewalls to form the enclosure.

10. The system of claim 1, wherein the angle is preselected in order to ensure that a sufficient amount of light from the light source will be reflected off of a reflective surface and back towards the image sensor during operation of the inspection device.

11. The system of claim 1, further comprising a reflective surface and a transparent surface arranged on the reflective surface, the reflective surface being configured to reflect light from the light source that enters the transparent surface back through the transparent surface and towards the inspection device.

12. The system of claim 1, further comprising a track to which the inspection device is attached, and wherein the inspection device is configured to me movable along the track in order to inspect seals a long a surface.

13. The system of claim 12, wherein the track is configured for attachment with a sealing device for creating the seal and the inspection device is arranged on the track in order to follow behind the sealing device and allow for inspection of the seal immediately after the seal is created by the sealing device.

14. The system of claim 13, further comprising the sealing device.

15. The system of claim 1, wherein the light source includes a light emitting diode (LED).

16. The system of claim 1, wherein the light source includes a light emitting diode (LED) strip.

17. The system of claim 1, wherein the at least one wing portion includes a first arm having a first end connected to the housing and a second end connected to a second arm, and wherein the first side surface and the second side surface are opposing sides of the second arm.

18. The system of claim 1, further comprising at least one second wing portion extending away from the housing from a second outer surface of one of the one or more sidewalls at a second angle such that a third side surface of the at least one second wing is oriented away from the one or more sidewalls and a fourth side surface of the at least one second wing is oriented towards the one or more sidewalls.

19. The system of claim 13, further comprising a second light source arranged on the fourth side surface.

20. The system of claim 1, wherein the image sensor includes a camera.

* * * * *